US010023652B2

(12) United States Patent
Hollingsworth et al.

(10) Patent No.: US 10,023,652 B2
(45) Date of Patent: Jul. 17, 2018

(54) METHOD OF TARGETING GLYCOPROTEINS TO TREAT CANCER

(71) Applicant: Board of Regents of the University of Nebraska, Lincoln, NE (US)

(72) Inventors: Michael Anthony Hollingsworth, Omaha, NE (US); Prakash Radhakrishnan, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 90 days.

(21) Appl. No.: 14/902,473

(22) PCT Filed: Jun. 24, 2014

(86) PCT No.: PCT/US2014/043793
§ 371 (c)(1),
(2) Date: Dec. 31, 2015

(87) PCT Pub. No.: WO2015/006043
PCT Pub. Date: Jan. 15, 2015

(65) Prior Publication Data
US 2016/0376376 A1 Dec. 29, 2016

Related U.S. Application Data

(60) Provisional application No. 61/844,226, filed on Jul. 9, 2013.

(51) Int. Cl.
| C07K 16/30 | (2006.01) |
| A61K 39/395 | (2006.01) |
| A61K 31/7068 | (2006.01) |
| A61K 31/519 | (2006.01) |
| A61K 31/513 | (2006.01) |
| A61K 31/4745 | (2006.01) |
| A61K 31/282 | (2006.01) |
| A61K 39/00 | (2006.01) |

(52) U.S. Cl.
CPC ........ *C07K 16/3092* (2013.01); *A61K 31/282* (2013.01); *A61K 31/4745* (2013.01); *A61K 31/513* (2013.01); *A61K 31/519* (2013.01); *A61K 31/7068* (2013.01); *A61K 39/39558* (2013.01); *A61K 2039/505* (2013.01); *C07K 2317/76* (2013.01)

(58) Field of Classification Search
None
See application file for complete search history.

(56) References Cited

U.S. PATENT DOCUMENTS

2008/0311134 A1* 12/2008 Junutula .......... A61K 47/48384
424/178.1
2009/0291075 A1 11/2009 Eng et al.
2013/0059744 A1 3/2013 Wandall et al.

OTHER PUBLICATIONS

Conroy et al. (Current Oncol. Rep. Jan. 23, 2013 15: 182-189).*
Abraxane®, (Prescribing Information Jul. 2015).*
Budiu et al., "Soluble MUC1 and serum MUC1-specific antibodies are potential prognostic biomarkers for platinum-resistant ovarian cancer," Cancer Immunol Immunother 60(7):975-84 (Jul. 2011).
Chen et al., "Microarray Glycoprofiling of CA125 improves differential diagnosis of ovarian cancer," J Proteome Res 12(3):1408-18 (Feb. 2013).
Da Silva et al., "A Novel MUC16 (CA125) Monoclonal Antibody," European Journal of Cancer 48(Suppl. 5):S42 (Jul. 2012).
Dharma et al., "Novel monoclonal antibodies against the proximal (carboxy-terminal) portions of MUC16," Appl Immunohistochem Mol Morphol 18(5):462-72 (Oct. 2010).
Fingert et al., "Clinical development of Ovarex Mab-B43.13 monoclonal antibody for treatment of ovarian cancer: impact of immune responses and circulating CA125 levels on clinical efficacy," European Journal of Cancer 37:S260 (Apr. 2001).
Marcos-Silva et al., "Characterization of binding epitopes of CA125 monoclonal antibodies," J Proteosome Res 13(7):3349-59 (Jun. 2014).
Marcos-Silva et al., "A novel monoclonal antibody to a defined peptide epitope in MUC16," Glycobiology 25(11):1172-82 (Jul. 2015).
Nustad et al., "CA125 (TD-1) report 4. Evaluation of five new antibodies using ascites-derived or recombinant single repeat (R11) CA125," Tumor Biology 27(Suppl. 2):13 (2006).
Schultes et al., "Induction of tumor- and CA125-specific T cell responses in patients (pts) with epithelial ovarian cancer (EOC) treated with OvaRex® Mab-B43.13," Proceedings of the American Association for Cancer Research 43:144 (Mar. 2002).
Sørensen et al., "Chemoenzymatically synthesized multimeric Tn/STn MUC1 glycopeptides elicit cancer-specific anti-MUC1 antibody responses and override tolerance," Glycobiology 16(2):96-107 (Oct. 2005).
Extended European Search Report for EP Application No. 14822065.0; dated May 31, 2016, pp. 1-12.
Hosein, et al., "A retrospective study of neoadjuvant Folfirinox in unresectable or border-line-resectable locally advanced pancreatic adenocarcinoma", BMC Cancer, 12:1-7 (2012).
Raina, et al., "Dependeance on the MUC1-C Oncoprotein in Non-Small Cell Lung Cancer Cells", Molecular Cancer Therapeutics, 10:806-816 (2011).
Remmers, et al., "Aberrant expression of mucin core proteins and O-linked glycans associated with progression of pancreatic cancer", Clinical Cancer Research 19:1981-1993 (2013).
Radhakrishnan, et al., Immature truncated O-glycophenotype of cancer directly induces oncogenic features. Proceedings of the National Academy of Sciences, 111, No. 39 (2014).
Celgene Safety Data Sheet, Celgene #21—Abraxane Powder for Suspension for Infusion, pp. 1-11, Oct. 6, 2011.

* cited by examiner

Primary Examiner — Peter J Reddig
(74) Attorney, Agent, or Firm — McDonnell Boehnen Hulbert & Berghoff LLP

(57) ABSTRACT

The present disclosure relates to a method of inhibiting tumor growth. More specifically, the present disclosure relates to the use of monoclonal antibodies for targeting truncated O-glycans on glycoproteins to inhibit activation of pro-survival cell signaling pathways, to inhibit tumor growth. For example, monoclonal antibody AR9.6 may be used to target truncated O-glycans on the MUC16 glycoprotein, thereby inhibiting the phosphatidylinositol 3-kinase/Akt (Pi3K/Akt) signaling pathway.

12 Claims, 13 Drawing Sheets

A

B

A

B

A

B

METHOD OF TARGETING GLYCOPROTEINS TO TREAT CANCER

CROSS-REFERENCE TO RELATED APPLICATIONS

This application is a US National Phase application under 35 USC § 371 of International Application PCT/US2014/043793, filed Jun. 24, 2014, which claims priority from and the benefit of U.S. Provisional Application No. 61/844,226, filed on Jul. 9, 2013, the specifications of which are hereby incorporated by reference in their entirety.

BACKGROUND

Field

The present disclosure relates to a method of treating cancer. More specifically, the present disclosure relates to the use of monoclonal antibodies for targeting truncated O-glycans on glycoproteins to inhibit activation of pro-survival cell signaling pathways. For example, monoclonal antibody ARM may be used to target truncated O-glycans on the MUC16 glycoprotein.

Related Prior Art

Pancreatic adenocarcinoma is the fourth-leading cause of cancer-related death in the United States with a 5 year survival rate of less than 4% and a median survival of less than 6 months. According to the American Cancer Society, the estimated number of new cases and deaths due to pancreatic cancer in the US in 2013 are 45,220 and 38,460, respectively. At the time of diagnosis more than 80% of pancreatic cancer patients have either locally advanced or highly metastatic disease.

Currently, Folfirinox is the first line of treatment for patients with metastatic disease and good performance status and gemcitabine alone or in combination with Abraxane is the first-line chemotherapeutic agent for the treatment of other patients with pancreatic adenocarcinoma. However, the response rate is modest, and median overall survival remains dismal. Poor patient response to chemotherapy and poor prognosis are due in part to constitutive activation of oncogenic signaling pathways that are associated with development of drug resistance, aggressive tumorigenicity and early metastasis.

These adverse effects result in a need for a novel molecularly targeted therapy to combat lethal cancers generally including, without limitation, pancreatic cancers.

It is well established that aberrant expression of membrane mucin MUC16 is associated with tumour progression and metastasis of cancers such as ovarian and pancreatic cancer. The role of MUC16 in tumour progression and metastasis occurs through interaction with oncogenic modulators. For instance, it is understood that aberrant expression of MUC16 in ovarian cancer cells facilitates peritoneal metastasis through interactions with mesothelin (tumour differentiation factor) and through immunosuppressive functions by blocking natural killer cell-mediated cytotoxicity, while overexpression of MUC16 increases breast cancer cell proliferation via stimulation of Janus kinase 2 (JAK2). It is also understood that MUC16 is upregulated in pancreatic cancers, and expression is increased in liver metastases—although expression of MUC16 was not detected in pancreatic intraepithelial neoplasia (PanIN) nor in normal pancreas, suggesting that expression of MUC16 may occur later in disease progression.

Despite the role of MUC16 in disease progression being known, little is known about a possible role of oligosaccharide (O-linked glycosylation) modifications on mucin type glycoproteins. Research shows that a higher percentage of truncated O-glycan (Tn and sialyl Tn, STn) expression occurs in pancreatic adenocarcinoma, relative to other types of carcinomas, and it is well established that aberrant expression of truncated O-glycans is associated with tumour progression and adverse patient outcome. For example, STn antigen is expressed by more than 80% of human carcinomas, and in all cases the detection of STn correlates with poor prognosis and decreased overall survival of patients. Further, expression of tumour associated truncated carbohydrate antigens Tn and STn mucin type glycoproteins are among the most common tumour-specific oligosaccharide alterations observed in adenocarcinomas. Appearance of Tn and STn epitopes on cancer cell surfaces are due to overexpression of ST6GalNAc-1 or lack of core 3 Synthase/ core 1 synthase activity and/or defects in Core 1 synthase specific molecular chaperone (Cosmc), Overexpression of STn antigen has been observed on many epithelial cancer cells, but the highest frequency is observed in pancreatic cancer. For example, overexpression of STn occurs early on in tumour progression on epithelial cancer cells (e.g. early epithelial benign lesions) and pancreatic cancer (e.g. pancreatic intraepithelial neoplasia stage III (PanIN-3)), which is a premalignant lesion thought to precede development of pancreatic adenocarcinoma. Altogether, these findings indicate that overexpression of truncated O-glycans is an early event leading to pancreatic cancer development. However, the exact biological mechanism of these truncated O-glycans during pancreatic tumorigenesis may not be well understood.

Notwithstanding over two decades of research, attempts to utilize known biomarkers of cancer, such as mucin-type O-glycans, in the development of molecularly targeted therapies for cancer have failed.

Therefore, there is a need for novel methods of using monoclonal antibodies that target O-glycans on mucin-type glycoproteins to inhibit activation of pro-survival cell signaling pathways.

SUMMARY

According to an embodiment, there is provided a method to inhibit tumor growth comprising administering to a subject in need thereof a monoclonal antibody to target an O-glycan mucin-type glycoprotein to inhibit activation of pro-survival cell signaling pathways.

The monoclonail antibody may be AR9.6.

The mucin-type glycoprotein may be MUC16.

The pro-survival cell signaling pathway may be the PI3K/Akt signaling pathway.

The O-glycan mucin-type glycoprotein may comprise a truncated O-glycan.

The truncated O-glycan may comprise a Tn antigen, a sialyl Tn antigen (STn), or a combination thereof.

The method of the present invention may further comprise administering a second therapeutic agent comprising at least one of a cytotoxic agent, an additional antibody or a therapeutically active fragment thereof, or a chemotherapy regimen.

The cytotoxic agent may be at least one of gemcitabine and abraxane.

The additional antibody or therapeutically active fragment thereof may be oregovomab antibody B43.13.

The chemotherapy regimen may be folfirinox.

The tumor may be chosen from a pancreatic tumor, a colon tumor, an ovarian tumor, a breast tumor, a lung tumor, and a liver tumor.

The method may be for the treatment of a cancer.

According to another embodiment, there is provided a pharmaceutical composition comprising a monoclonal antibody to target an O-glycan mucin-type glycoprotein, in combination with a pharmaceutically acceptable carrier.

The monoclonal antibody may be AR9.6.

The mucin-type glycoprotein in MUC16.

The pharmaceutical composition may further comprise a second therapeutic agent comprising at least one of a cytotoxic agent, an additional antibody or a therapeutically active fragment thereof, or a chemotherapy regimen.

The cytotoxic agent may be at least one of gemcitabine and abraxane.

The additional antibody or therapeutically active fragment thereof may be oregovomab antibody B43.13.

The chemotherapy regimen may be folfirinox.

According to another embodiment, there is provided a method of inhibiting tumor growth comprising administering to a subject in need thereof a pharmaceutical composition of the present invention.

The method may be for the treatment of a cancer.

According to another embodiment, there is provided a use of a monoclonal antibody that targets an O-glycan mucin-type glycoprotein to inhibit activation of pro-survival cell signaling pathways for inhibiting tumor growth, The monoclonal antibody may be AR9.6.

The mucin-type glycoprotein may be MUC16.

The pro-survival cell signaling pathway may be the PI3K/Akt pathway.

The O-glycan mucin-type glycoproteins may comprise a truncated O-glycan.

The use of claim 22, wherein the truncated O-glycan comprises a Tn antigen, a sialyl Tn antigen (STn), or a combination thereof.

The use may further comprise the use of a second therapeutic agent selected from at least one of a cytotoxic agent, an additional antibody or a therapeutically active fragment thereof, or a chemotherapy regimen.

The cytotoxic agent may be at least one of gemcitabine and abraxane.

The additional antibody or therapeutically active fragment thereof may be oregovomab antibody B43.13.

The chemotherapy regimen may be folfirinox.

The cancer may be chosen from a pancreatic, tumor, a colon tumor, an ovarian tumor, a breast tumor, a lung tumor, and a liver tumor.

The use may be for the treatment of cancer.

According to another embodiment, there is provided a use of a composition of the present invention for inhibiting tumor growth.

The use may be for the treatment of cancer.

The following terms are defined below.

The terms "administration of" and/or "administering a" is intended to mean providing an antibody according to the present invention with or without additional compound(s) to a subject in need of treatment.

The term "composition" intended to mean a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the pharmaceutically acceptable carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing an antibody according to the present invention and a pharmaceutically acceptable carrier. By "pharmaceutically acceptable" it is meant the carrier, diluent or excipient must be compatible with the other ingredients of the formulation and not deleterious to the recipient thereof.

The term "chemotherapy regimen" is intended to mean combination of several chemotherapeutic agents. The rationale behind such chemotherapy regimen is that different chemotherapy drugs work through different cytotoxic mechanisms, and that the results of using multiple drugs will be synergistic to some extent. Because they have different dose-limiting adverse effects, they can be given together at full doses in chemotherapy regimens. Chemotherapy regimen may include induction and maintenance regimen.

The term "induction regimen" is intended to mean a chemotherapy regimen used for the initial treatment of a disease.

The term "maintenance regimen" is intended to mean the ongoing use of chemotherapy to reduce the chances of a cancer recurring or to prevent an existing cancer from continuing to grow.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 98 shows that treatment of Capan-1 cosmc KO cells with HER2 inhibitor (CP724714, at 24 h) inhibits the phosphorylation of Akt (S473) in a dose dependent manner.

FIGS. 12A and 128 show AR9.6 mAb epitope mapping. AR9.6 mAb binds to a conformational epitope on MUC16 TR (SEA domain 5 and 6) without glycosylation. MUC16 TR1.7 contains pad of the linker region of TR4, SEA domain 5, entire TR5 linker region and half of the SEA domain of TR6 (12,660-12,993, 264 aa). MUC16 TR 1.2 contains part of the linker region of TR4, SEA domain 5 and TR5 linker region (12,665-12,858, 194 aa). MUC16 5/2 TR construct contains half of the SEA domain 5, TR5 linker region and SEA domain of TR6 (12,757-12,923, 167 aa).

DETAILED DESCRIPTION

Figure 1:
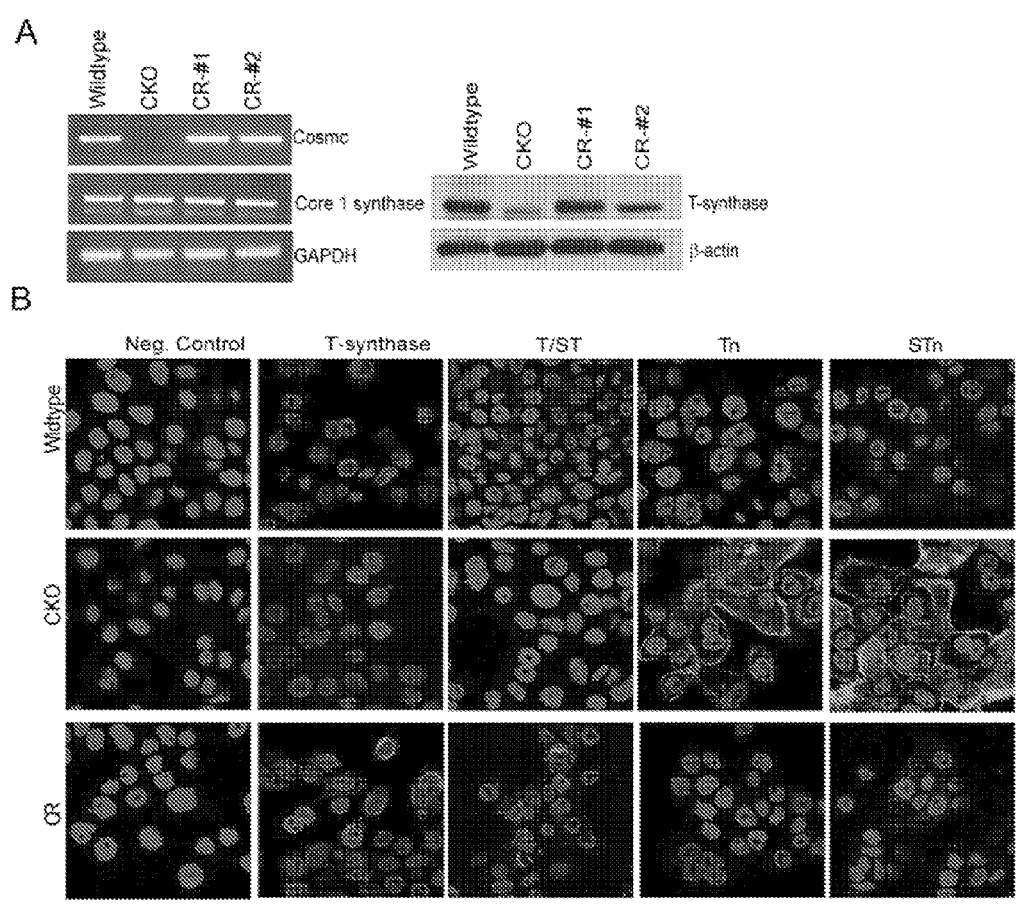
FIGS. 1A and 1B show Generation of truncated O-glycans in pancreatic cancer cells. Genetic knockout of COSMC in pancreatic cancer cell line (1A) showed expression of truncated O-glycans (Tn and STn) (1B) through destabilizing the core 1 synthase enzyme activity (1A-B). Re-expression of Cosmc diminishes the formation of truncated O-glycans (1B) through stabilizing the core 1 synthase enzyme activity (1A-B).

In embodiments, there is disclosed a novel method for treating cancer. More specifically, a novel method for use of monoclonal antibodies to target truncated O-glycans on mucin-type glycoproteins to inhibit activation of pro-survival cell signaling pathways, is provided. According to an embodiment of the present invention, targeting truncated mucin-type glycoproteins inhibits their role in tumourgenicity and tumor progression.

In one embodiment, a therapeutically effective amount of the monoclonal antibody AR9.6 may be used to target truncated O-glycans on the MUC16 glycoprotein, thereby inhibiting the phosphatidylinositol 3-kinase/Akt (PI3K/Akt) signaling pathway.

The present method teaches, amongst other things, that cancer specific truncation of O-glycans on the MUC16 glycoprotein (also known as CA125) creates a ligand for Her2/Neu (also known as ErbB2) receptors, which results in an oncogenic signaling cascade through Akt that increases the oncogenic potential of cancer cells. This method provides that in addition to serving as a biomarker for carcinomas, aberrant glycoforms of MUC16 can serve as a form of oncogenic cytokine.

MUC16 is a membrane bound, heavily glycosylated, cell surface glycoprotein that is expressed in normal epithelium of endometrium, trachea and cornea. The expression of MUC16 is also often upregulated in malignant tumours that also produce circulating soluble forms of MUC16. It is known that aberrant expression of membrane mucin MUC16 is associated with tumourigenicity and metastasis of cancers, such as pancreatic cancer. Further, MUC16 is not detected in pancreatic intraepithelial neoplasia (PanIN) and increased in primary tumors and metastatic lesions, suggesting that expression of this mucin is a later event in disease progression, Aberrant expression of MUC16 in ovarian cancer cells facilitates peritoneal metastasis through interactions with mesothelin (a tumor differentiation factor) and through immunosuppressive functions by blocking natural killer cell-mediated cytotoxicity. A recent study also showed that overexpression of MUC16 increases breast cancer cell proliferation via stimulation of Janus Kinase 2 (JAK2). These reports strongly suggest that MUC16 plays a major role in tumor progression and metastasis through interaction with oncogenic modulators. Therefore, research suggests that MUC16 plays a major role in cancer through interaction with oncogenic modulators, however little has been done to study oligosaccharide (O-linked glycosylation) modification on mucin-type glycoproteins such as MUC16, particularly as a potential cancer therapy.

It is contemplated that the present method and therapeutic strategies may be used alone or in combination with cytotoxic agents to increase overall patient survival. The cytotoxic agents include, but are not limited to, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoids/deltoids plant alkaloids, proteasome inhibitors, HSP-90 inhibitors, histone deacetylase inhibitors (HDAC) inhibitors, purine analogs, pyrimidine analogs, MEK inhibitors, CDK inhibitors, ErbB2 receptor inhibitors, mTOR inhibitors and combinations thereof as well as other antitumor agents.

Angiogenesis inhibitors include, but are not limited to, EGFR inhibitors, PDGFR inhibitors, VEGFR inhibitors, TTE2 inhibitors, IGFIR inhibitors, matrix metalloproteinase 2 (MMP-2) inhibitors, matrix metalloproteinase 9 (MMP-9) inhibitors, thrombospondin analogs such as thrombospondin-1 and N-Ac-Sar-Gly-Val-D-allolle-Thr-Nva-He-Arg-Pro-NHCH2CH3 or a salt thereof and analogues of N-Ac-Sar-Gly-Val-D-allolle-Thr-Nva-lle-Arg-PrO-NHCH2CH3 such as N-Ac-GlyVal-D-alle-Ser-Gln-lle-Arg-ProNHCH2CH3 or salt thereof.

Examples of EGFR inhibitors include, but are not limited to, Iressa (gefitinib), Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), ABT-869 and angiozyme.

Examples of thrombospondin analogs include, but are not limited to. TSP-I and ABT-510.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib) and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl-1H-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Exambles of ErbB2 receptor inhibitors include, but are not limited to, CP-724-714, CI-1033, (canertinib), Herceptin (trastuzumab), Omitarg (2C4, petuzumab), TAK-165, GW-572016 (Ionafamib), GW-282974, EKB-569, PI-166, dHER2 (HER2 Vaccine), APC8024 (HER2 Vaccine), anti-HER/2neu bispecific antibody, B7.her2IgG3, AS HER2 tri-functional bispecfic antibodies, mAB AR-209 and mAB 2B-1.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, giufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine ocfosfate, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin. EICAR, hydroxyurea and deferoxamine.

Examples of antibiotics include intercalating antibiotics but are not limited to, aclarubicin, actinomycins such as actinomycin D, amrubicin, annamycin, adriamycin, bleomycin a, bleomycin b, daunorubicin, doxorubicin, elsamitrucin, epirbucin, glarbuicin, idarubicin, rnitornycin C, nernorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, diflomotecan, irinotecan HCL (Camptosar), edotecarin, epirubicin (Ellence), etoposide, exatecan, girnatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab, Bevacizumab, Trastuzimab, specific CD40 antibodies and specific IGFIR antibodies, Examples of hormonal therapies include, but are not limited to, exernestane (Aromasin), leuprolide acetate, anastrozole (Arirnidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoids/deltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFGI), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil, Floxuridine, Doxifluridine, Ratitrexed, cytarabine (ara C), Cytosine arabinoside, Fludarabine, and Gemcitabine.

Examples of purine analogs include but are not limited to, Mercaptopurine and thioguanine.

Examples of antimitotic agents include, but are not limited to, ABT-751, paclitaxel, docetaxel, epothilone D (KOS-862) and ZK-EPO.

Compounds of the present invention are also intended to be used as a radiosensitizer that enhances the efficacy of radiotherapy, Examples of radiotherapy include but are not limited to, external beam radiotherapy (XBRT), or teletherapy, brachtherapy or sealed source radiotherapy, and unsealed source radiotherapy.

Compounds of the present invention can also be used in combination with a different class of Bcl-2 inhibitors, such as ABT263 or ABT737.

The present method will be further described by way of the following examples.

The present invention will be more readily understood by referring to the following examples which are given to illustrate the invention rather than to limit its scope.

EXAMPLE 1

Role of TN/STN Epitope-Containing Glycoproteins in Pathogenesis of Pancreatic Cancer A first experiment is performed to evaluate the role of Tn/STn epitope-containing glycoproteins in the pathogenesis of pancreatic cancer. Appearance of Tn and STn epitopes on cancer cell surfaces is due to the overexpression of the ST6GalNAc-1 gene, to lack of core 3 synthase/core 1 synthase activity and/or defects in core 1 synthase-specific molecular chaperone "Cosmc". In this experiment, a universal and stable genetic engineering strategy that creates truncated O-glycans on cancer cell surfaces (SimpleCells) is used. The method comprises the use of a human pancreatic cancer cell line in which the Cosmc locus, a molecular chaperone for the enzyme core 1 synthase that controls O-glycan elongation, is deleted using Zinc Finger Nuclease (ZFN) technology to limit the O-glycan epitopes to Tn and STn.

Having regard to FIG. 1, Cosmc knockout (KO) in Capan-1 cells generates truncated O-glycans on cancer cell surfaces through degradation of core 1 synthase. Re-expression of Cosmc (CR) on this cell line elongates the Tn epitopes through restoring the core 1 synthase enzyme activity. Also, similar results were observed in isogenic OVCAR-3, Colo205 and HepG2 cancer cells (data not shown). These results suggest that COSPIC knockout in cancer cells causes' constitutive expression of tumor associated truncated carbohydrate antigens (Tn and STn) on the cancer cell surface. Capan-1 Cosmc re-expressing cells, clone no. 1 has been used for the rest of the study.

EXAMPLE 2

Role of Truncated O-Glycans on Pancreatic Cell Tumourigenicity

A second experiment is performed to investigate the role of truncated O-glycans on pancreatic cell tumourigenicity. The cells are evaluated for oncogenic and metastatic potential in an orthotopic transplantation model.

Figure 2:
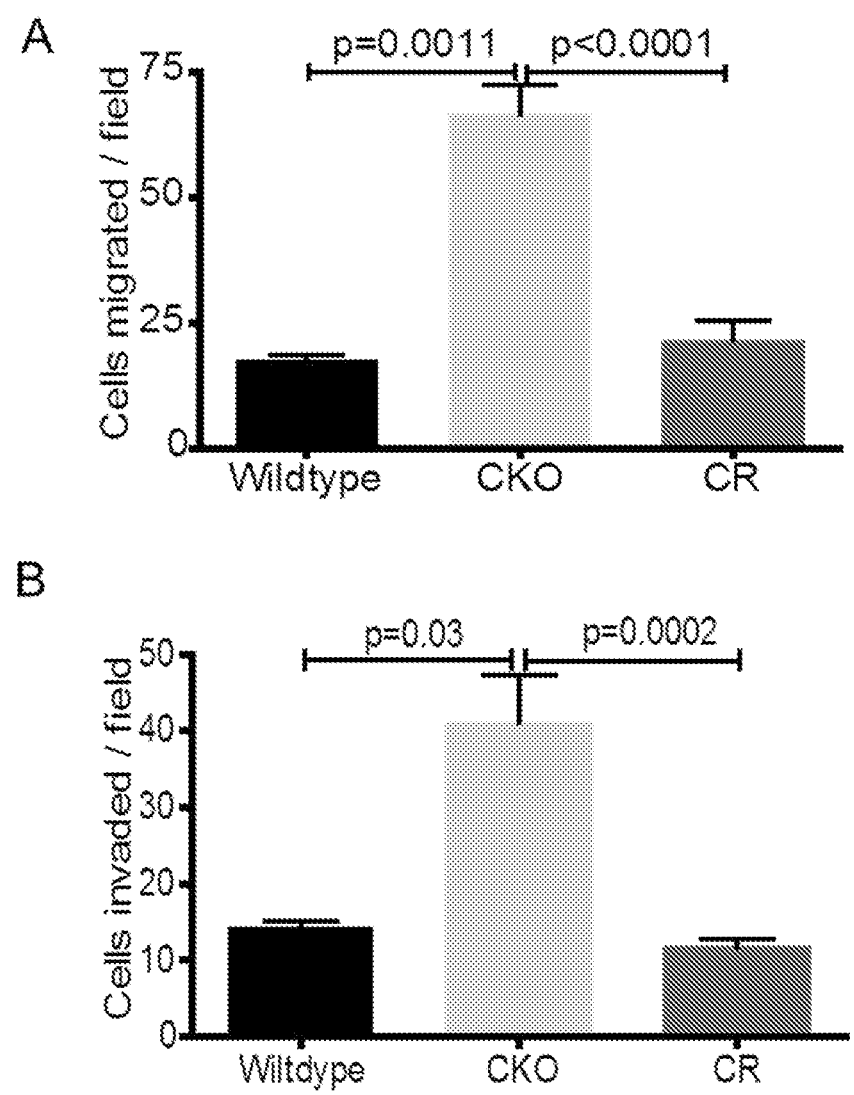
FIG. 2A shows Cosmc knockout cells increased in vitro migration (2A) and FIG. 2B invasion (2B). Re-expression of Cosmc restores this effect.
Figure 3:
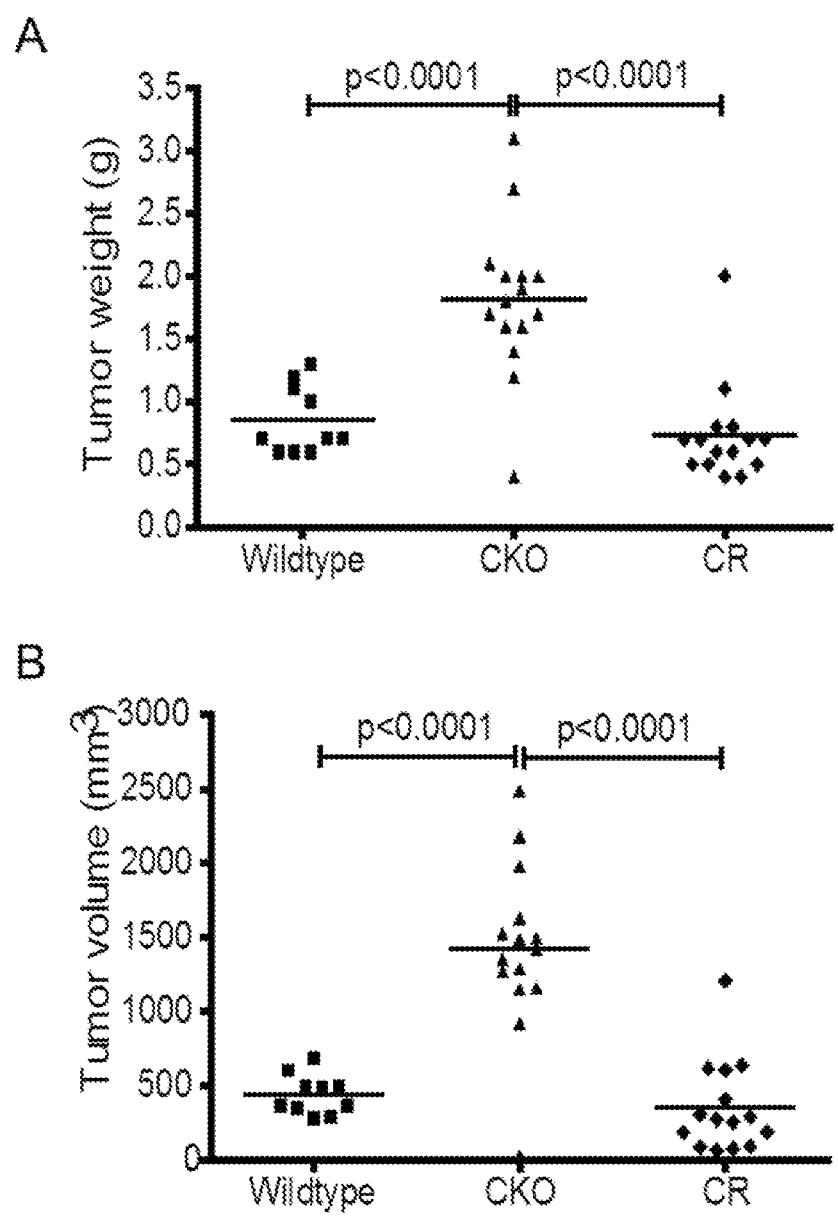
FIG. 3 shows Cosmc knockout cells increased tumour weight (3A) and volume (3B) in an in vivo orthotopic pancreatic cancer mouse model. Re-expression of COSMC restores this effect.

Having regard to FIGS. 2A and 2B, expression of truncated O-glycans in pancreatic Capan-1 cells resulted in increased in vitro migration (using a polyethylene terephthalate membrane assay, FIG. 2A) and invasion (Boydon chambers assay, FIG. 2B), when compared to parental and cosmc re-expressing cells. Having regard to FIGS. 3A and 3B, significantly increased tumour weight and volume is observed in cosmc-deleted cells grown in an in vivo orthotopic pancreas tumour model.

In summary, cosmc-deleted cells expressing Tn/STn epitopes showed significantly increased in vitro migration, invasion and in vivo tumour growth, and metastatic properties compared to parental cells.

EXAMPLE 3

Phospho-Kinome Analysis

Figure 4:
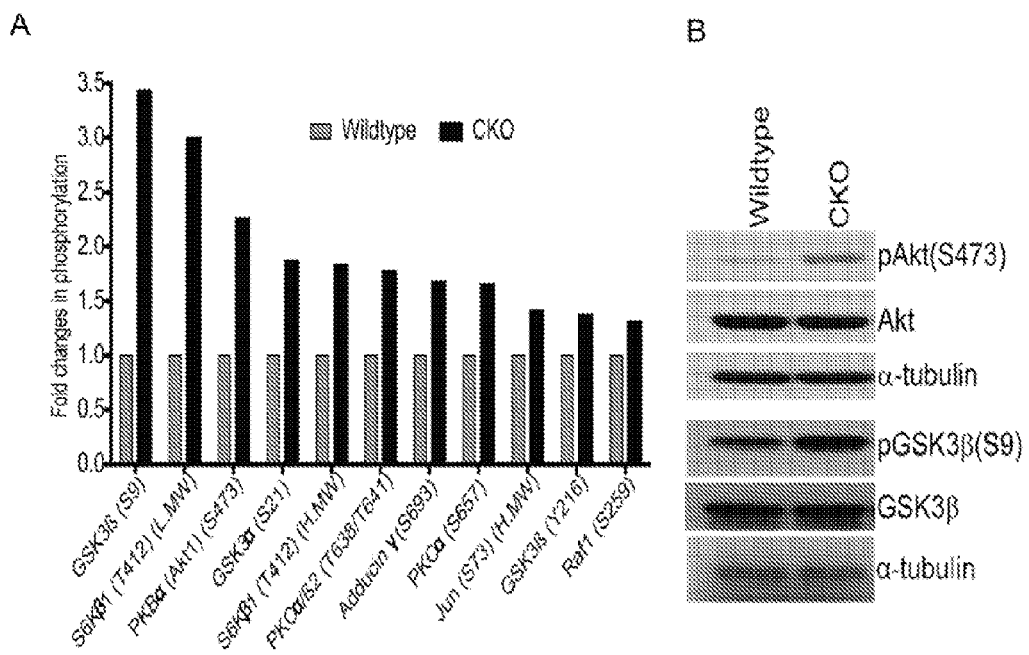
FIG. 4A shows phosphoprotein expression in Capan-1 wild type and CKO cells. Increased phosphorylation of GSK3, Akt, S6Kb1, PKCa, Adducin, Jun and Raf1 in CKO cells. The relative folds change for phosphoproteins in CKO cells (counts per minute, CPM) were normalized to the levels in the wild type cells.
FIG. 4B shows phospho-immunoblotting conducted on parental and Cosmc KO cells to validate p-AKT and PGSK3b.
Figure 5:
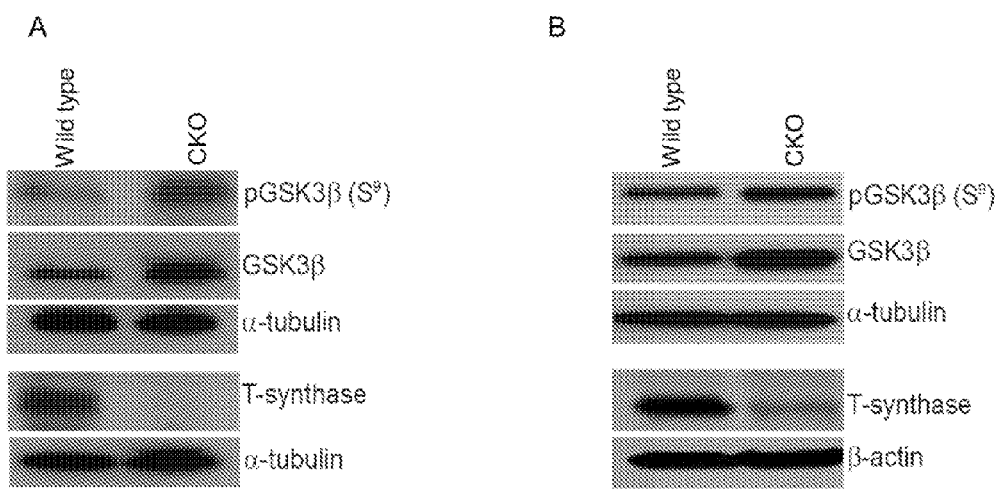
FIG. 5 shows validation of PGSK3b and T-synthase in parental and Cosmc KO cells of OVCAR-3 (Ovarian carcinoma) and HepG2 cells (hepatocarcinoma).

In order to further investigate the possibility that cell signaling mechanism are affected by aberrant glycosylation of cell surface receptors or their ligands, a focused analysis of phosphoprotein expression has been performed (n=38) in isogenic Capan-1 cell lines using the Kinetworks KPSS-1.3 Screen. The phospho kinorne screen shows selective upregulation of nine phosphoproteins (measured by counts per minute, CPM) PKBα/Akt1 ($S^{473}$ and $T^{308}$), GSK3β ($S^9$ and $Y^{216}$), S6Kb1, GSK3α ($S^{21}$), PKCα/β2, PKCα, Adducin γ, PKCα, Jun ($S^{73}$) and Raf1, and down-regulation of seven phosphoproteins Msk1, PKCδ, MEK1/2, B23, Smad1/5/8, Jun (S73, two low molecular weight), and Erk1 in Cosmc KO cells compared to parental cells with at least 24% change (the median range from the average of the duplicate is ±12) (FIG. 4A). The upregulated phosphoproteins CPM values of CKO cells are normalized with wild type cells CPM values, and represented as fold changes in phosphorylation (FIG. 4A). Selected phospho proteins (pAkt and pGSK) levels are confirmed and validated by western blot analysis in isogenic Capan-1 cells (FIG. 48). Phosphorylation of Akt at T308 is increased over the baseline in Capan-1 CKO cells, but the exact percentage could not be calculated, because of the baseline phosphorylation at this site in parental cells is not detectable. Also, these results are confirmed and validated in other isogenic cancer cell lines (OVCAR-3 and HepG2) (FIG. 5). These results demonstrate that expression of Tn/STn antigens in cancer cells activates phosphatidylinositol 3-kinase/Akt (PI3K/Akt) oncogenic signaling pathways in PC cells.

EXAMPLE 4

Truncated O-Glycans Mediated Altered Global Gene Expression

To evaluate if the truncated O-glycan expression affects global gene expression levels in CKO pancreatic cancer cells. RNA sequencing and Ingenuity pathway analysis (IPA) has been performed.

Figure 6:
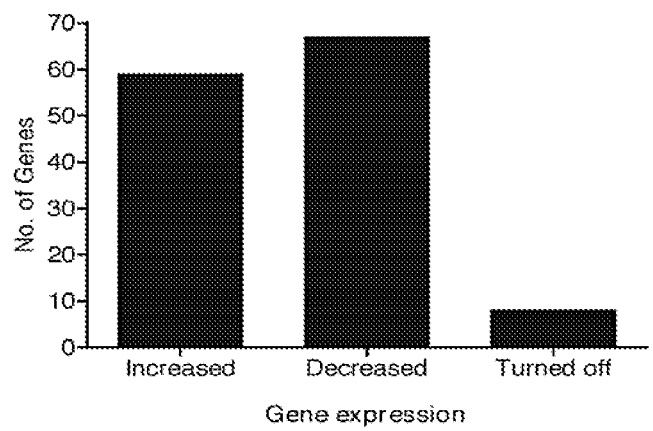
FIG. 6A shows RNA sequencing analysis of differentially expressed genes between Capan-1 wild type and CKO cells with >2 fold change.
FIG. 6B shows that a majority of the differentially expressed genes are associated with cancer (n=72, 37%).
Figure 6:
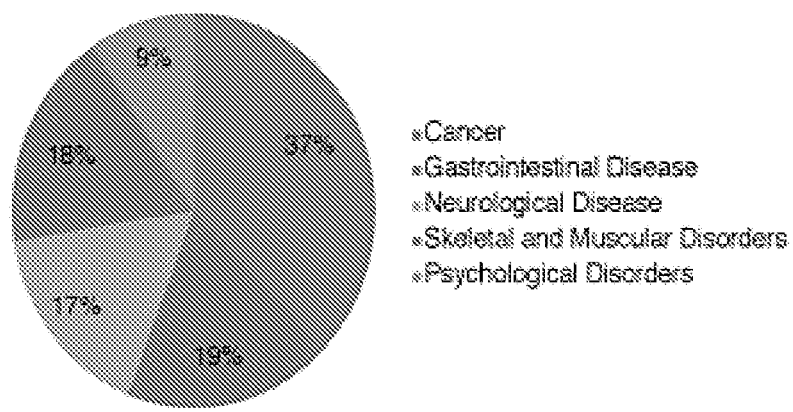
Figure 7:
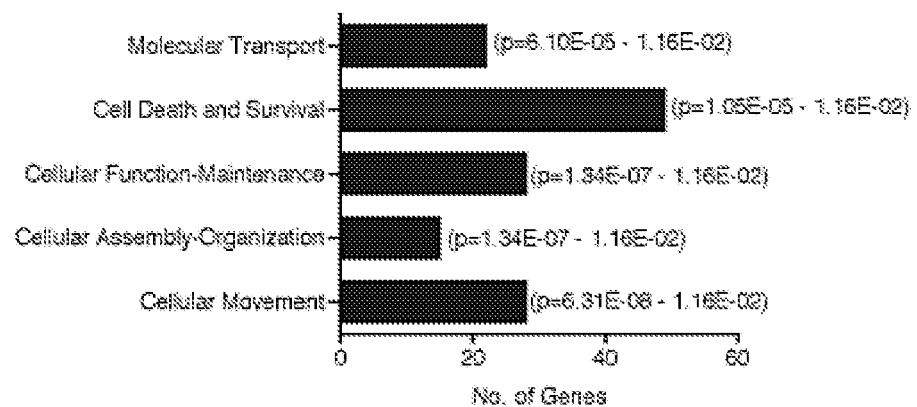
FIG. 7A shows that IPA analysis on differentially expressed genes by molecular and cellular functions showed 49 genes are associated with cell death and survival, and 28 genes are associated with cellular movement.
FIG. 7B shows validation of mRNA levels of selected differentially expressed genes (from RNA seq. results) by qRT-PCR. The relative expression values (n-fold change) of IGFBP5, FGFG19, LIF, SPP1, SPDEF. MUC2, C130RF15, TNC, DAPK1 and MUTYH is calculated by normalized (with GAPDH) values of CKO cells over wild type cells. Each point represents mean± S.D. of triplicate determinants of the three independent experiments. [*; $p<0.0005$, ; $p<0.005$,*; $p<0.05$, ns; non-significant].
Figure 7:
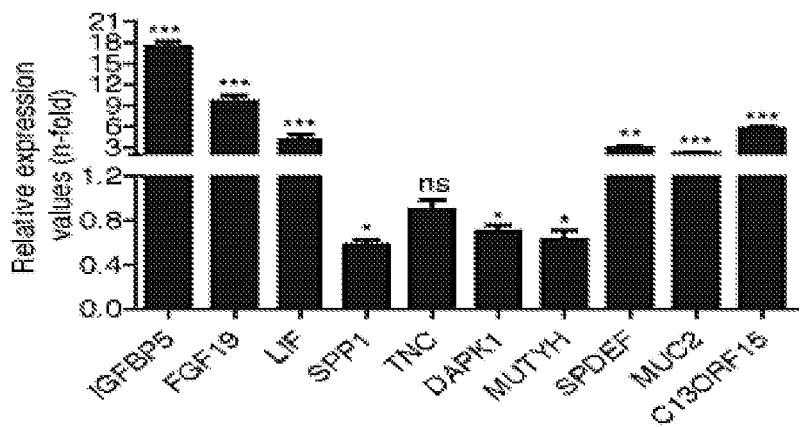

RNA sequencing analysis showed 59 genes are upregulated and 67 genes were down regulated by >2 fold changes and 8 genes were silenced in CKO cells compared to wild cells (FIG. 6A). Furthermore, when classified based on diseases and disorders, a majority of the differentially expressed genes is associated with cancer (n=72, 37%) (FIG. 6B). The majority of differentially expressed genes were associated with cell death and survival, and cellular movement functions (FIG. 7A). The mRNA levels of selected tumor enhancer genes in CKO cells (compared to wild type cells), are validated by quantitative Real-time PCR analysis. The up-regulated genes MUC2, SPDEF, LIF, C13ORF15, FGF19, and IGFBP5 in COSMC KO cells showed (2.20, 2.85, 4.21, 5.59, 9.56 and 17.36) fold difference by qRT-PCR and (3.42, 2.48, 2.74, 2.48, 3.00 and 6.04) fold difference by RNA sequencing as compared to wild type cells. The down-regulated genes DAPK1 and MUTYH in COSMC KO cells showed (1.4 and 1.6) fold difference by qRT-PCR and (2.0 and 2.1) difference by RNA sequencing as compared to wild type cells. Altogether, these results suggest that the aberrant expression of truncated O-glycans on the cancer cell surface modulates the expression of genes whose function is associated with tumor promotion.

EXAMPLE 5

Ingenuity Pathway Analysis (IPA)

To identify the upstream receptor-ligand interactions that activate the observed oncogenic cell signaling pathways (PI3K/Akt) in truncated O-glycan expressing PC cells, a network analysis on these differentially phosphorylated proteins (29 out of 38) is performed by using Ingenuity pathway analysis (IPA).

TABLE 1

| Disease and Disorders Diseases and Disorders | | |
| --- | --- | --- |
| Name | p-value | # Molecules |
| Cancer | 6.37E−11-3.92E−04 | 15 ← |
| Developmental Disorder | 1.50E−09-3.21E−04 | 12 |
| Neurological Disease | 4.03E−08-3.82E−04 | 11 |
| Organismal Injury and abnormalities | 4.03E−08-3.16E−04 | 12 |
| Cardiovascular Disease | 1.73E−07-3.21E−04 | 12 |

TABLE 2

| Top Canonical pathways Top Canonical Pathways | | |
| --- | --- | --- |
| Name | p-value | Ratio |
| Molecular Mechanisms of Cancer | 1.4E−16 | 12/381 (0.031) |
| B Cell Receptor Signaling | 3.04E−16 | 10/171 (0.058) |

TABLE 2-continued

| Top Canonical pathways Top Canonical Pathways | | |
| --- | --- | --- |
| Name | p-value | Ratio |
| ErbB2-ErbB3 Signaling | 6.56E−16 | 8/60 (0.133) ← |
| 14-3-3-mediated Signaling | 2.05E−15 | 9/121 (0.074) |
| Prostate Cancer Signaling | 1.54E−14 | 8/99 (0.081) |

The IPA revealed that a significant number of cancer pathways (Table 1) are affected by Cosmc knockout in PC cells. Notably among these is activation of epidermal growth factor receptor (ErbB2-ErbB3) signaling pathways in CKO cells (Table 2). Signal transduction by these EGF receptors depends on receptor dimerization. Several studies have reported that ErbB2-ErbB3 dimerization on the cancer cell surface activates PI3K/Akt oncogenic cell signaling pathways in cancers including pancreatic cancer. These results suggested that activation of PI3K/Akt oncogenic cell signaling occurs via activation of EGF receptors on truncated O-glycan expressing PC cells.

Figure 8:
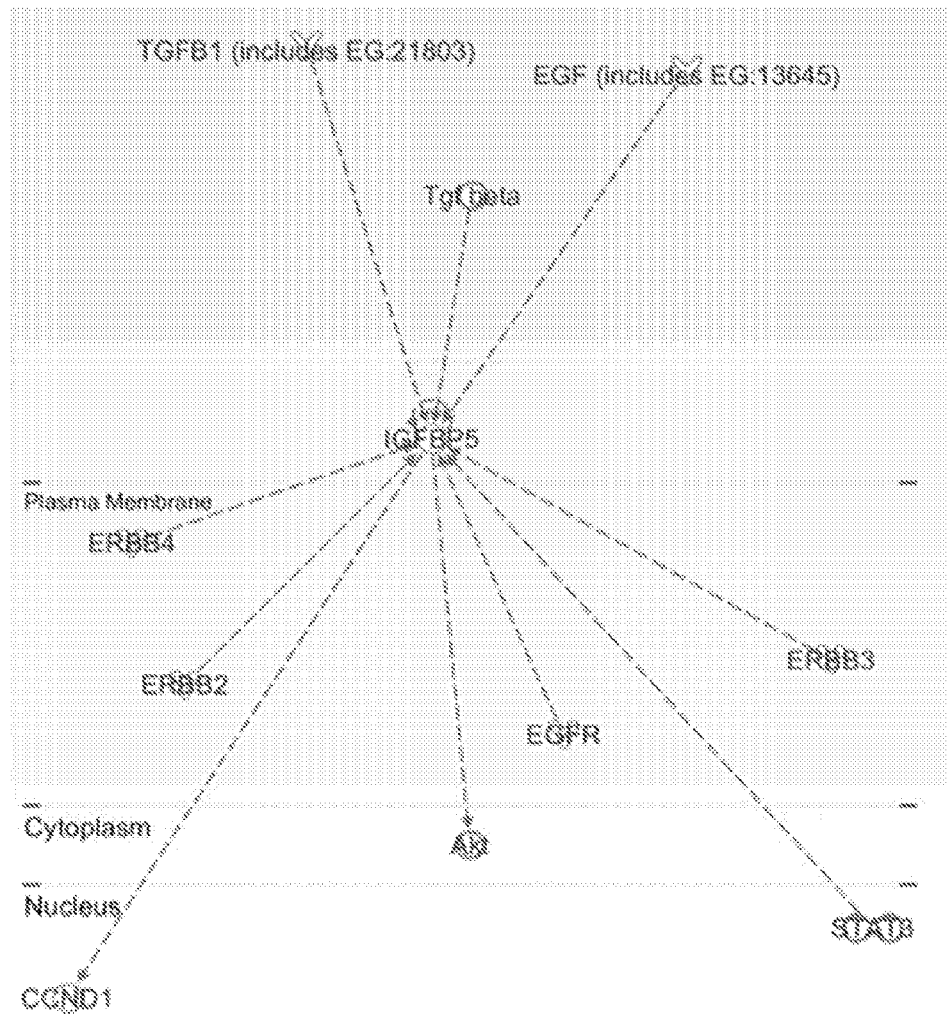
FIG. 8 shows ingenuity pathway analysis on RNA sequencing data. IPA on one of the highly upregulated gene, IGFBP5 in CKO cells compared to wild type Capan-1 cells. IGFBP5 is tightly regulated by ErbB family members.

Similarly, a network analysis is performed of all of the upregulated genes in CKO cells by conducting IPA. The network analysis revealed that IGFBP5 (Insulin like growth factor binding protein 5) gene expression (6 fold up by RNA sequencing and 17.6 fold up by qRT-PCR) is tightly regulated by EGF family receptors (EGFR1 2, 3 and 4) (FIG. 8). Similarly, another gene, SPDEF (a transcription factor) was also controlled by EGFR2 (data not shown). The combined results of RNA seq. and IPA demonstrate that expression of truncated O-glycans on cancer cells activate EGF receptors family member to induce downstream oncogenic cell signaling pathways, which lead to enhanced tumorigenesis in CKO PC cells.

EXAMPLE 6

Activation of Her2 and its Downstream Akt Signaling Pathways

It is known that the phosphatidylinositol 3-kinase/Akt (PI3K/Akt) signaling pathway is a potentially oncogenic signaling pathway that mediates cellular processes, including cell proliferation, growth, motility and cell survival. Increased Akt activity has been mainly associated with cell survival through effects on numerous downstream targets, including the inactivation of pro-apoptotic proteins, activation of anti-apoptotic genes and the progression of the cell cycle. Indeed, activation of Akt is associated with poor prognosis in pancreatic cancer (e.g. studies show that 59% of pancreatic adenocarcinomas displayed hyperactivation of Akt).

Next, it was invest gated whether O-glycan-expressing cells activate the PI3K/Akt signaling pathway. This activation may be via interactions with MUC4, the Tn antigen on MUC4, or MUC16 with the ErbB-2 receptor. These mucin-growth factor receptor interactions may differentially regulate the expression of genes with oncogenic (i.e. upregulation) and tumour suppression (i.e. down regulation) functions.

Figure 9:
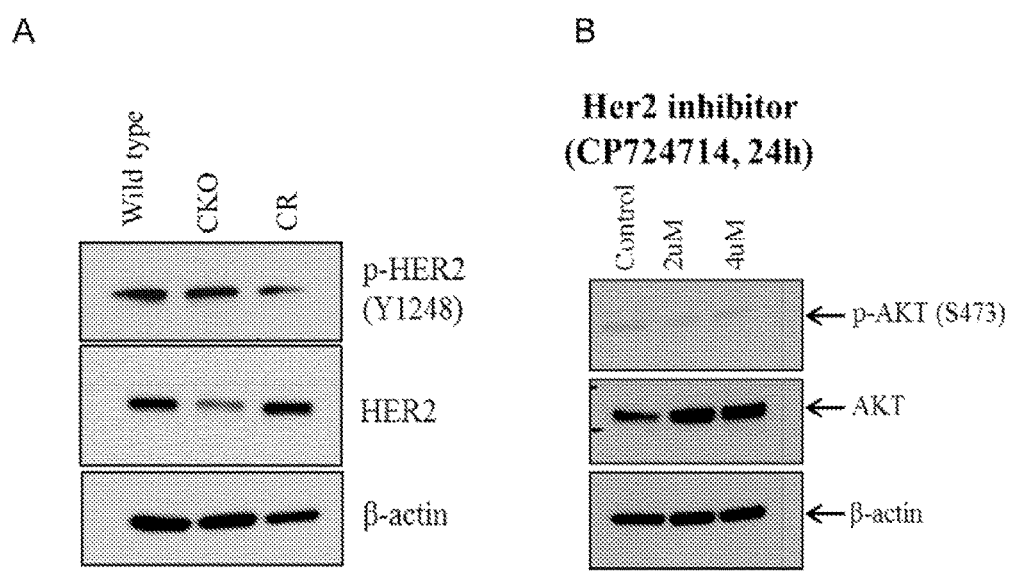
FIG. 9A shows increased phosphorylation of ErbB2/EGFR21HER2 (Y1248) is observed in Cosmc KO cells.

Having regard to FIG. 9, overexpression of truncated O-glycans on mucin type glycoproteins enhances the activation of ErbB2 receptors through either binding or induction of heterodimerization among the receptor family members. Increased phosphorylation of HER2 (Y1248) is observed in Cosmc KO cells as compared to wild type and Cosmc re-expression cells (FIG. 9A). Further, treatment of Cosmc KO cells with a small molecule HER2 inhibitor (CP724714), decreases the phosphorylation of Akt in a dose dependent manner (FIG. 9B). These results suggest that expression of truncated O-glycans constitutively activates HER2/Akt oncogenic signaling pathways in Cosmc KO cells.

EXAMPLE 7

Figure 10:
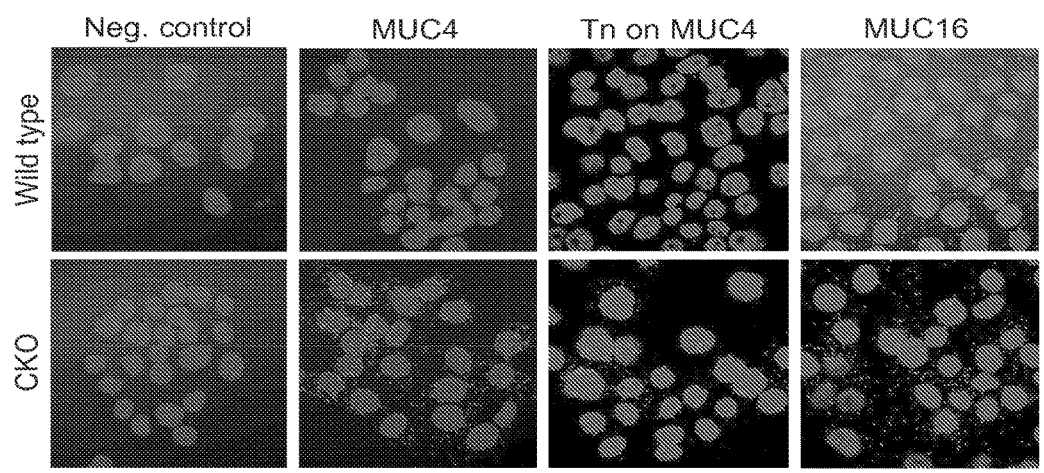
FIG. 10A shows a proximity ligation assay (PLA) showing the increased interaction between MUC16 and ErbB2 observed in Cosmc KO cells and parental (wild type) Capan-1 cells.
FIG. 10B shows a proximity ligation assay (PLA) showing the increased interaction between MUC16 and ErbB2 observed in Cosmc KO cells and parental (wild type) Capan-1 cells.
Figure 10:
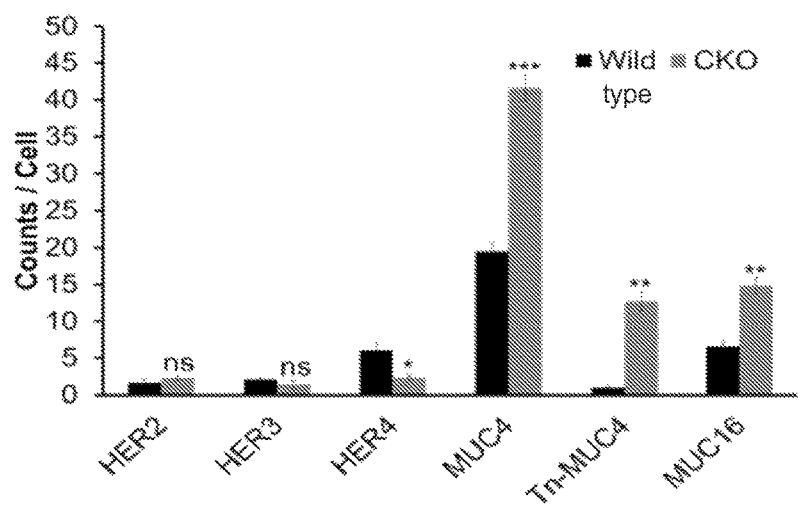

Protein-Protein Interaction Between Her2 and other Egfr Family Members And Mucins To investigate EGF receptor dimerization and activation status, protein-protein interaction studies are performed by Proximity ligation assay (PLA) on Capan-1 wild type and CKO cells. PLA is routinely used to identify protein-protein interactions by using protein specific antibodies. Using this method interactions are identified between growth factor receptors EGFR2 (ErbB2), EGFR3 (ErbB3), EGFR4 (ErbB4), and between these growth factor receptors and mucin molecules, MUC1, MUC4, Tn-on MUC4 and MUC16. Importantly, significantly increased interactions of EGFR2 with MUC4, Tn-on MUC4 and MUC16 were observed in CKO cells compared to the parental cells (FIG. 10A-B). However, no significant changes are observed in either homo or heterodimerization of EGF receptors between wild type and CKO Capan-1 cells. These results demonstrate that MUC4, Tn-MUC4 and MUC16 interact with EGFR2/ErbB2 and activate PI3K/Akt signaling cascades in truncated O-glycan expressing cancer cells.

EXAMPLE 8

MUC16 Specific Monoclonal Antibody (MAB) Ar9.6 Inhibits Akt Phosphorylation

To directly define whether the mucin-EGF receptor interaction activated downstream Akt phosphorylation CKO pancreatic cells, an antibody blocking assays is performed. Wild type and CKO cells are treated with monoclonal antibodies (mAb) specific to MUC1 and MUC16. MUC1 antibody did not induce detectable changes in the Akt phosphorylation (data not shown). However, treatment of Capan-1 wild type cells with anti-MUC16 antibodies (5E11, B43.13 and AR9.6), inhibited the basal level activation of Akt (S473) (due to minimal amounts of truncated O-glycans on the cancer cell surface as part of the natural tumor progression) and only AR9.6 mAb (2.5 and 5 µg/ml) significantly decreased the constitutively hyper phosphorylated Akt (S473) (due to constitutive expression of truncated O-glycans) at 24 h when compared to control and IgG treated CKO cells (FIG. 11A). Also, similar effects were observed in OVCAR-3 isogenic cells (FIG. 11B). These results suggest that the interaction between MUC16 and EGF receptors activates oncogenic cell survival signaling cascades in truncated O-glycan expressing PC cells.

Figure 11:
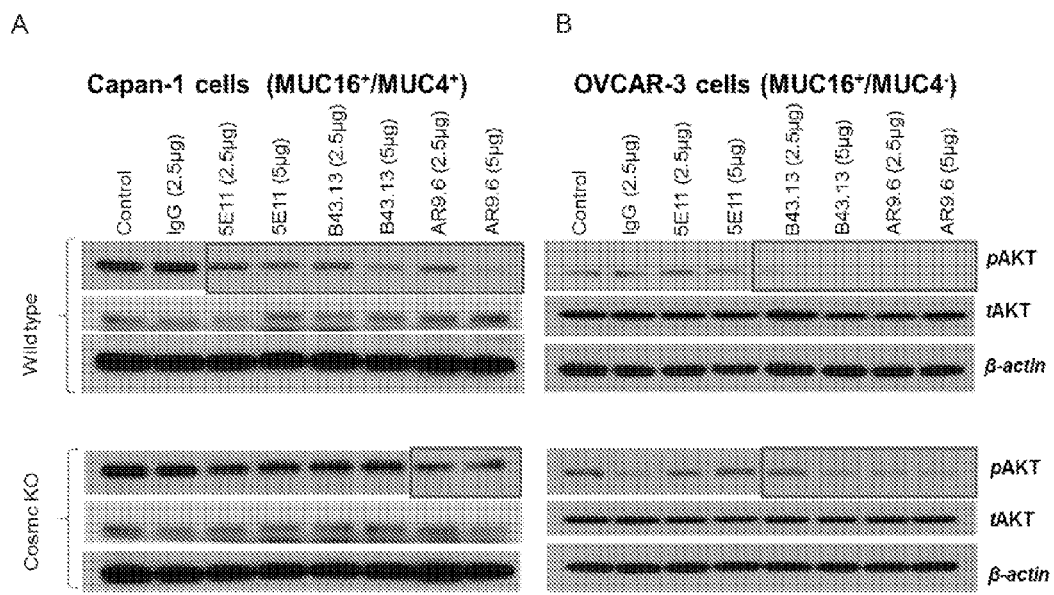
FIG. 11 shows the treatment of Capan-1 (A) and OVCAR-3 (B) cells with MUC16 specific antibodies. After 24 h time points, cell lysate is probed for Akt phosphorylation in wild type and CKO cells by immunoblotting.

Having regard to FIG. 11, MUC16-specific mAb AR9.6 caused a significant decrease in phosphorylation of Akt at 24 hour time points with 2.5 and 5 µg/ml concentrations when compared to control and IgG treated cells. As such, AR9.6 appears to target the ligand itself, rather than the growth receptors, and appears thereby capable of binding with cell surface associated glycoproteins, or circulating glycoproteins. Therefore, the method of the present invention may potentially be used to treat cancer in a manner similar to already proven targets such as, for example, Her2/Neu/EGF etc, although through different mechanisms.

AR9.6 has originally been made to recognize the MUC16 protein in the form of ovarian cancer antigen CA125, despite being significantly different from oregovomab antibody B43.13. The B43.13 antibody does not recognize the truncated O-glycans form of MUC16.

Figure 13:
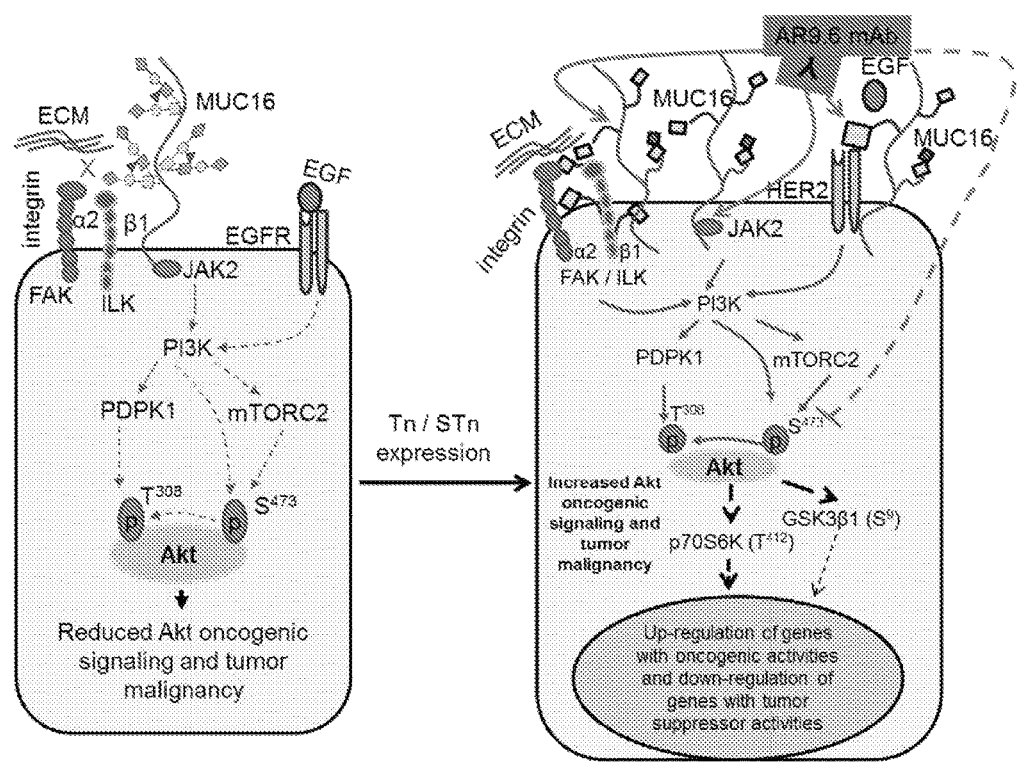
FIG. 13 shows a summary of the present method. Expression of Truncated O-Glycans on MUC16 enhances the pancreatic cancer cell malignant properties by activating oncogenic cell signaling.

In summary, MUC16-specific mAb (AR9.6) exhibits significant inhibition of PI3K/Akt pathway. These results suggest that ARM may block MUC16-ErbB2 interaction, thereby inhibiting activation of that pro-survival signaling pathway. Thus, truncated O-glycans on mucin type glycoproteins (MUC16) constitutively activate oncogenic survival signaling through ErbB2 receptors and thereby enhances the tumourigenicity of pancreatic cells. An overall summary of the results are provided in FIG. 13.

EXAMPLE 9

AR9.6 MAB Epitope Mapping

Figure 12:
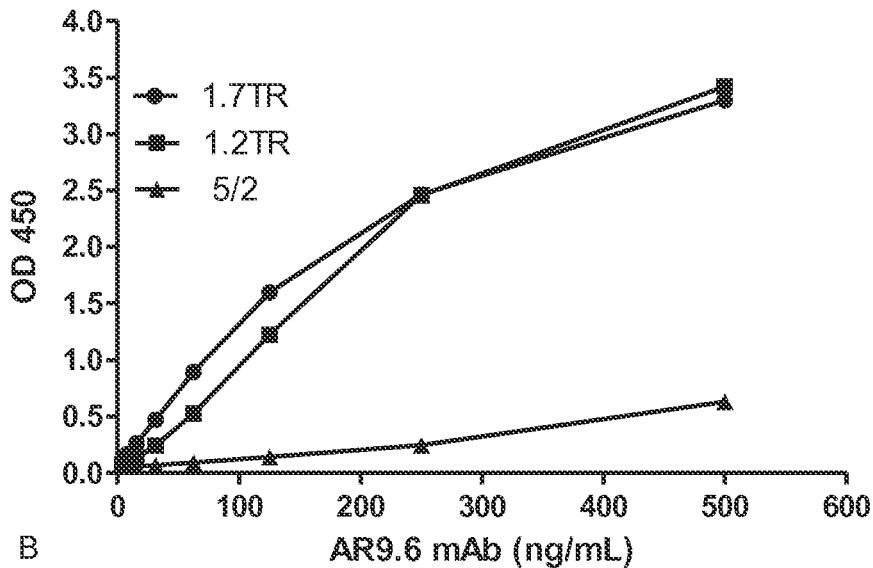
Figure 12:
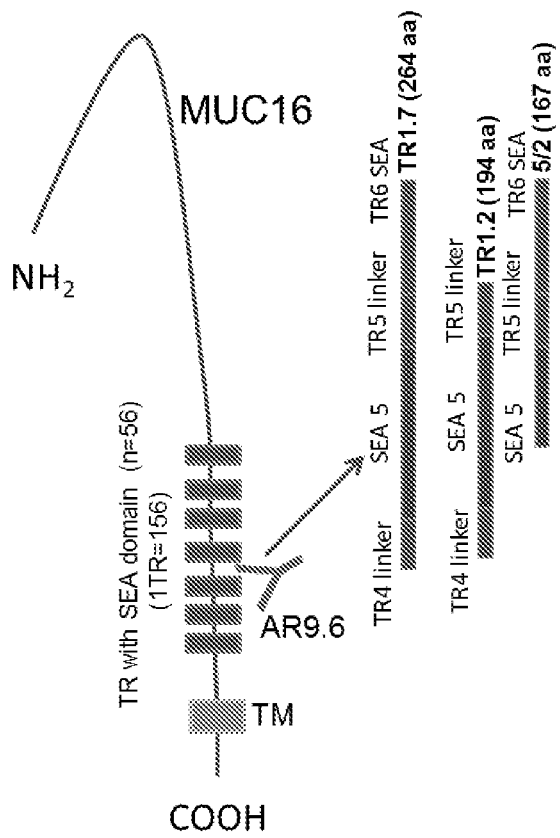

Next, an ELISA experiment is performed to find out the AR9.6 mAb binding site on MUC16. Different MUC16 tandem repeat (TR) containing SEA domains are incubated with increasing concentration of AR9.6 mAb. MUC16 TR1.7 contains part of the linker region of TR4, SEA domain 5, entire TR5 linker region and half of the SEA domain of TR6 (12,660-12,993, 264 aa). MUC16 TR 1.2 contains part of the linker region of TR4, SEA domain 5 and TR5 linker region (12,665-12,858, 194 aa). MUC16 5/2 TR construct contains half of the SEA domain 5, TR5 linker region and SEA domain of TR6 (12,757-12,923, 167 aa). All these construct were expressed in Rosetta 2(DE3) cells. Increased reactivity of AR9.6 mAb with MUC16 1.7 TR and MUC16 1.2 TR is observed than compared to MUC16 5/2 TR containing sequences (FIG. 12A-B). These results suggest that AR9.6 mAb binds to a conformational epitope MUC16 TR without glycosylation. However, it is unknown if glycosylation affects these bindings.

EXAMPLE 10

Combination Therapy with AR9.6 and Gemcitabine

A combination therapy against lethal pancreatic cancer by targeting disease specific MUC16 with mAb AR9.6 in combination with gemcitabine is discussed.

The previous examples and preliminary observations suggested the use of MUC16-specific mAb such as AR9.6 mAb to target disease-specific forms of MUC16 along with gemcitabine to combat highly metastatic pancreatic cancer. Recent studies also showed that targeted therapy alone or in combination with cytotoxic agents significantly improved overall patient survival. For example, treatment of ovarian cancer patients with MUC16-specific mAb (B43.13 or OVArex) alone and breast cancer patients with ErbB2-specific mAb (Herceptin) along with cytotoxic agents showed significant improvement in overall patient survival.

According to an embodiment, MUC16-specific mAb AR.9.6 in combination with gemcitabine treatment against pancreatic cancer may provide a highly effective treatment approach, and may satisfy the current need to develop therapeutic strategies which may improve patient drug response and overall survival.

The present example suggests that a combination therapy of MUC16-specific mAb such as AR9.6 mAb along with gemcitabine treatment may reduce growth and metastasis of pancreatic cancer. In this regard, MUC16-specific mAb such as AR9.6, and the combination of MUC16-specific mAb such as AR9.6 with gemcitabine, may impact upon malignant properties and oncogenic signaling in human pancreatic cancer cell lines in vitro. Parental and Cosmc knockout (truncated O-glycan expressing) pancreatic cancer cell lines may be treated with MUC16-specific mAb such as AR9.6 mAb, Gemcitabine or MUC16-specific mAb such as AR9.6 mAb and gemcitabine in combination to evaluate the potential of treatment with antibody alone and in combination with chemotherapy to inhibit malignant properties of the tumor cells. In addition, the capacity of this therapy to affect oncogenic cell signaling pathways (PI3K/Akt) may be analyzed.

Additionally, MUC16-specific mAb such as AR9.6 mAb may effectively impact upon gemcitabine treatment in an in vivo orthotopic pancreatic cancer model. An orthotopic tumor model of pancreatic cancer may be used in severe combined immunodeficient mice. Mice may be treated with MUC16-specific mAb such as AR9.6 mAb. Gemcitabine or a combination for one or two therapeutic cycles. Tumor growth may be monitored by imaging with a near-IR in vivo imager (PEARL) using IRDye 800CW 2deoxygluycose. Tumor progression and overall survival may be monitored at various time points. In vivo proliferation index and apoptosis may be analyzed by Immunohistochemistry and TUNEL assay, respectively.

According to an embodiment of the present invention, it is disclosed herein that the aberrant expression of truncated O-glycans on mucin-type glycoproteins and overexpression of MUC16 has been associated with tumor progression and metastasis of pancreatic cancer, and thus, targeting these disease-specific forms of truncated O-glycan containing MUC16 with AR9.6 mAb and gemcitabine should inhibit tumor cell growth. According to an embodiment, truncated O-glycan expressing pancreatic cancer cells may be treated with MUC16-specific mAb, such as AR9.6 along with gemcitabine. MU16 and ErbB2/Her2-positive pancreatic cancer cells for AR9.6 mAb, Gemcitabine, combinations of AR9.6 mAb and gemcitabine treatment may be explored. Cell viability and apoptosis may be analyzed by fluorescent based alamar blue assays and Live/Dead cell assays, respectively. Changes in the cell signaling pathways (PI3K/Akt axis) can be evaluated. Inhibition of cancer cell migration and invasion by AR9.6 mAb and gemcitabine combination can be carried out by using polyethylene terephthalate (PET) membrane and Boyden chamber assays, respectively.

Pancreatic cancer cell lines Caran-1 and Colo357 (parental and Cosmc KO) cells can be treated with different concentrations of AR9.6 mAb alone, Gemcitabine alone, and a combination of both agents at different time points to measure cell viability using fluorescent based alamar blue assay as described in Radhakrishnan P., et al. Clin Cancer Res 2013 Apr 15;19(8):2025-35. Treatment of cells with phosphate buffered saline and antibody isotype IgG can serve as a control for the above mentioned treatments. Dose-response curves may be evaluated by using the National Cancer Institute (NCI) algorithm: Tz¼ number of control cells at time t0, C¼ number of control cells at time t, and T¼ number of treated cells at time t; 100×[(T−Tz)/(C−Tz)]. These experiments can be repeated at least three times and statistical analysis may be conducted using unpaired Student t test.

Apoptosis induced by AR9.6 mAb, Gemcitabine and combinations of both can be analyzed in parental and Cosmc KO Capan-1 and Colo357 cells using Live/Dead Cell Assay Kit (Invitrogen) as described in Radhakrishnan P., et al. Clin Cancer Res 2013 Apr 15:19(8):2025-35. Treatment of cells with phosphate buffered saline and antibody isotype IgG can serve as a control for the above mentioned treatments. Cell viability (live/dead) can be determined by fluorescence microscopy by counting live (green) and dead (red) cells. Experiments can be repeated 3 times and Student's t test may be used to determine the significance. In addition to Live/Dead cell assay, it may also be investigated the activation of apoptotic pathway initiators and executors such as caspase 3, 8 and 9 through caspase activation assays or immunoblotting using pro-caspase specific antibodies (shows intact and cleaved capases).

Since activation of ErbB2-PI3K/Akt signaling pathways affects cell migration and invasion of cancer cells, migration and invasion analysis of PC cells treated with AR9.6 mAb, Gemcitabine alone Cr combination both agents may be done using polyethylene terephthalate membrane and matrigel (500 μg/filter) coated poly carbonate filters (12-mm pore size; Becton Dickinson) as described previously in Radhakrishnan P., et al. Olin Cancer Res 2013 Apr 15;19(8):2025-35. Cells that traverse the membrane and matrigel can be stained with a Diff-Quick cell staining kit (Dade Behring, Inc). Cells in 6 fields/well can be counted at ×100 magnification and expressed as the average number of cells/field of view. Three independent measurements can be performed in each case. The data may be represented as mean of three independent measurements ±SD.

Activation of GSK3b, Akt, S6K and PKCa in Cosmc KO Capan-1 cells compared to parental cells can occur, and thus the MUC16-ErbB2 interactions mediated activation of PI3K/Akt and its downstream signaling effectors on either AR9.6 mAb or Gemcitabine alone or combinations of both agents treated PC cells can be explored. Untreated and treated Capan-1 and Colo357 parental and Cosmc KO cell lysates can be analyzed for inactivation/unphosphorylation of PI3K and Akt proteins by immunoblotting using phospho-PI3 Kinase p85 (Ty458)/p55 (Tyr199) and phospho-Akt (Thr308 and Ser473) antibodies. Activated Akt is a major regulator of cell survival, cell cycle progression and proliferation signaling cascades through activation or inactivation of the downstream proteins by post-translational modifications such as phosphorylation. Therefore, we may analyze phosphorylation of proteins (GSK3b, $p21^{Clip1}$, $p27^{Kip1}$ and cyclin D1) which are associated with cell proliferation and cell cycle progression function by immunoblotting using phospho-GSK3b (Ser9), phospho-p21 (Thr145 and Ser146), phospho-p27 (Thr157) and cyclin D1 specific antibodies. Also, proteins (Bad and XIAP), that are associated with cell survival can be evaluated by immunoblotting using phospho-Bad (Ser 136), phospho-XIAP (Ser87) specific antibodies.

It is hypothesized that inhibition of MUC16-ErbB2 interaction can reduce PI3K/Akt activation and its downstream signaling effectors in cells that are treated with AR9.6 mAb alone or in combination gemcitabine. AR9.6 mAb treatment may provide significant inhibition on PI3K/Akt signaling axis or alternatively, other pathways such as the possibility that MUC16 activates the JAK2 signaling pathway. Akt also enhances cancer cell survival by transcriptional regulation of anti-apoptotic gene expression through activation of transcriptional factor, cyclic-AMP response element binding protein (CREB). The expression of anti-apoptotic genes (including Bcl-2) mRNA expression can be quantified by real time-PCR analysis of parental and Cosmc KO cells treated with AR9.6 mAb alone or in combination with gemcitabine. A skilled person would know that such in vitro involve routine assays in the laboratory. One-way ANOVA and unpaired Student's t test can be used to determine whether there is a significant difference between control and different treatment groups. The difference can be considered significant only when p<0.05.

Targeted treatment with mAb in conjunction with cytotoxic chemotherapy has been an important research area during the last decade. This therapeutic approach holds promise for improved outcomes in patients with pancreatic cancer. Treatment of PC cells with AR9.6 mAb showed inhibition of PI3K/Akt survival signaling pathway through altering the mucin-growth factor receptor interactions suggesting that pretreatment of cancer cells with AR9.6 mAb can potentiate the anti-tumorigenic effect of gemcitabine through inhibition of constitutively active survival pathway. The working idea of this aim is to demonstrate the potentiation effect of AR9.6 mAb on gemcitabine treatment in an orthotopic pancreatic cancer model. An in vivo orthotopic tumor model of pancreatic cancer in severe combined immunodeficient mice (control and treated with AR9.6 mAb, Gemcitabine and alone and in combination) can be explored. Tumor growth (volume) can be monitored using the pearl Impulse in vivo imager. Time to tumor progression and overall survival can be evaluated, along with in vivo proliferation and apoptosis by immunohistochemistry and TUNEL assays.

Truncated O-glycan expressing pancreatic cancer cells can be orthotopically implanted into the mouse pancreas as described by Derosier LC, et al. Mol Cancer Ther 2007 Dec;6(12 Pt 1):3198-207. Briefly, mice can be anesthetized with i.p injection of xylazine-ketamine HCl solution. A small incision can be made on the left upper abdomen and the pancreas can be exposed by retraction of the spleen. Pancreatic cancer cells ($0.1$-$0.5 \times 10^6$ in 30-40 μl) may be injected into the pancreas using 27 gauge needle. The abdomen can be closed using 2-layer of suture with chromic catgut and ethilon suture. After 2-3 weeks of implantation, tumor growth can be measured by Pearl Impulse in vivo imager by using 2-Deoxy Glucose conjugated with IRDye 800CW and then animals may be randomized to different therapeutic arms.

After 2-3 weeks of tumor cell implantation, animals can be assigned to the following groups (n=15 mice per group): Untreated (vehicle control PBS, Group 1), AR9.6 alone (100 μg i.p on days 22, 26, 29 and 33 post-implant, Group 2), Gemcitabine alone (60 mg/kg i.p on days 23 and 30 post-implant, Group 3), combination of AR9.6 (100 μg i.p on days 22, 26, 29 and 33 post-implant) and Gemcitabine (60 mg/kg i.p on days 23 and 30 post-implant) (Group 4), combination of AR9.6 (100 μg i.p on days 25, 28, 32, 35, 53, 56, 60 and 63 post-implant) and Gemcitabine (60 mg/kg i.p on days 26, 33, 54 and 62 post-implant) (Group 5). Mice can be subjected to additional in vivo imaging and the tumor areas can be calculated on post-implant days 41, 72 and 83.

Tumor areas can be calculated for all mice in the treatment groups in each therapy study and compared with those from the initial (pre-therapy) in vivo imaging examination. A Kriskal-Wallis test can be used to determine differences between the groups in terms of changes in tumor volume following treatment. A p value of less than 0.05 can be considered statistically significant. The Wilcoxon rank sum test (with normal approximation) can be used for pairwise comparisons. Further, animals may be followed for survival, with tumor being documented when mice died, or at the time of sacrifice according to the University of Nebraska Medical Center Institutional Animal Care and Use Committee-approved protocol. A log rank test may be used to compare survival between the groups. The Kaplan-Meier method may be used to generate the survival curves. Metastasis of the tumors to other organs may be examined by both macroscopically and microscopically.

Tumor tissues (Group 1-4) from the above studies can be used for analysis of apoptosis by terminal nucleotidyl transferase-mediated nick end labeling (TUNEL) assay and Caspase 3 activation by immunohistochemistry. Further, in vivo proliferation index can be analyzed by immunohistochemical staining of anti-Ki 67 (proliferation marker) as described previously in Radhakrishnan P., et al. Olin Cancer Res 2013 Apr 15;19(8):2025-35. The tissue staining intensity may be given a composite score based on intensity and extent of tissue staining. The intensity may be graded on a four point scale: −, +, ++, and +++. These values may be given a numeric Score—[0], +[1], ++[2], and +++[3]. The extent of staining may be graded on a four-point scale: 1 (0-24%), 2 (25-49%), 3 (50-74%), and 4 (75-100%). The composite score may be obtained by multiplying the two values together and may range from 0-12. The values between the groups will be compared by one-way ANOVA and unpaired Student's t test.

Targeted therapy combining monoclonal antibody and cytotoxic agents could provide better overall survival among cancer patients. Therefore, significantly increased time to tumor progression and survival in mice treated with AR9.6 mAb and gemcitabine combination therapy relative to either agent alone may be provided. Similarly, significantly increased apoptosis and a reduced proliferation index in tumor tissues from combination therapy may be provided. Furthermore, significantly reduced metastasis in animals treated with AR9.6 alone or in combination with gemcitabine may be provided. Significant changes in the metastatic profile between control and treated animals can also be investigated based on the observed response. For example, if decreased peritoneal seeding and metastasis occurs, the possibility that MUC16 and mesothelin interaction influence development of peritoneal metastasis can be evaluated by analyzing the level of MUC16 in the peritoneal fluids (using ELISA by MUC16 specific antibodies) and MUC16 and mesothelin interaction in the peritoneal tumor tissues by immunofluorescence (using MUC16 and mesothelin specific antibodies). If the proposed AR9.6 mAb treatment does not significantly improve overall survival or metastatic activity, dose escalation studies can be performed and the schedule of administration of antibody can be altered to fully investigate the anti-tumorigenic potential and cytotoxicity effects AR9.6 mAb alone or combination with gemcitabine in the in vivo orthotopic tumor model system. If problems with imaging with the IRdye 800CW conjugated 2Deoxy Glucose arise, STri antigen specific mAb TKH-2 conjugated IRdye 800CW could also be used. An orthotopic pancreatic model is known and screening of multiple antitumor agents against pancreatic cancer in this model system have been performed.

Truncated O-glycan containing MUC16 is a disease specific target in pancreatic cancer and targeting against this with mAb AR9.6 along with gemcitabine combination may improve overall survival. Additional chemotherapeutic approaches such as FOLFIRINOX in combination with AR9.6 may also be contemplated, or another antibody to MUC16 (for example B43.13) in combination with gemcitabine to identify alternative therapeutic treatment to combat lethal pancreatic cancer. In addition, human pancreatic cancer tumor tissues can also be evaluated for levels of MUC16, MUC16-ErbB2 interaction and correlative activation of oncogenic signaling pathways in the same tissues.

Several studies have shown that aberrant expressions of truncated O-glycans are associated with tumor progression and adverse patient outcome. Moreover, STn antigen is overexpressed in pancreatic cancer precursor lesions PanIN-3, strongly suggesting that these truncated O-glycans are important for pancreatic cancer progression and early metastasis. Our preliminary data indicate that overexpression of truncated O-glycans enhances the tumorigenicity of pancreatic cancer cells by activating oncogenic signaling through ErbB2 receptors. Treatment of truncated O-glycan-expressing cells with MUC16-specific mAb AR9.6 significantly reduces the activation of oncogenic signaling pathway. Therefore, the combinatory therapy may be investigated (AR9.6 plus gemcitabine) against highly aggressive pancreatic cancer cells. The studies provided are highly innovative and novel because AR9.6 and gemcitabine combination therapy against pancreatic cancer cells has never been studied before.

Multiple studies have been reported that highest frequency of STn antigen expression is observed in pancreatic cancer among all other cancer. Extension of these truncated O-glycans by ectopic expression of Core 3 synthase resulted in suppression of pancreatic cancer cells tumor growth and metastasis, suggesting that oligosaccharide modifications influence the activity of proteins that mediate oncogenic, tumor suppressor, and metastatic cellular activities and thereby dramatically affect the progression and biological properties of tumors. Further, enhanced tumorigenicity in truncated O-glycans expressing pancreatic cancer cells through activation of oncogenic survival signaling pathways has been observed. Treatment of truncated O-glycan expressing cells with MUC16-specific mAb AR9.6 showed inhibition of phosphorylation of PI3K/Akt signaling pathway (see above). These data demonstrate that truncated O-glycans on MUC16 enhance pancreatic cancer tumorigenicity. Therefore, AR9.6 mAb and gemcitabine combination therapy in an in vivo orthotopic pancreas tumor model system can be evaluated to determine the antitumor potential of these therapeutic combinations. The preclinical data obtained from this study could lead to a novel therapeutic approach for pancreatic cancer, and more importantly, could provide critical information for advancing towards the long-term goal of developing novel targeted therapeutic strategies and to help to improve overall survival of pancreatic cancer patients.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for inhibiting growth of a tumor expressing glycoprotein MUC16 in a subject in need thereof, comprising administering to the subject a monoclonal antibody AR9.6 that binds to a tandem repeat 5 and 6 of MUC16 without glycosylation, in combination with a pharmaceutically acceptable carrier; and wherein the tumor is a pancreatic tumor, a colon tumor, an ovarian tumor, a breast tumor, or a liver tumor.

2. The method of claim 1, further comprising administering a second therapeutic agent, a cytotoxic agent, an additional antibody or a therapeutically active fragment thereof, and/or at least one chemotherapy agent.

3. The method of claim 2, wherein the cytotoxic agent is gemcitabine or albumin-bound paclitaxel.

4. The method of claim 2, wherein the additional antibody or the therapeutically active fragment thereof is oregovomab antibody B43.13.

5. The method of claim 2, wherein the chemotherapy agent is folfirinox.

6. A pharmaceutical composition for inhibiting growth of a tumor expressing glycoprotein MUC16 in a subject in need thereof, comprising:
   (a) a monoclonal antibody AR9.6 that binds to a tandem repeat 5 and 6 of MUC 16 without glycosylation and a cytotoxic agent or a chemotherapy agent in combination with a pharmaceutically acceptable carrier; or
   (b) the monoclonal antibody AR9.6 that binds to the tandem repeat 5 and 6 of MUC 16 without glycosylation, the cytotoxic agent, and the chemotherapy agent in combination with the pharmaceutically acceptable carrier;
   wherein the tumor is a pancreatic tumor, a colon tumor, an ovarian tumor, a breast tumor, or a liver tumor.

7. The pharmaceutical composition of claim 6, wherein the cytotoxic agent is gemcitabine or albumin-bound paclitaxel.

8. The pharmaceutical composition of claim 6, wherein the chemotherapy agent is folfirinox.

9. The pharmaceutical composition of claim 6, further comprising an additional antibody or a therapeutically active fragment thereof.

10. The pharmaceutical composition of claim 9, wherein the additional antibody or the therapeutically active fragment thereof is oregovomab antibody B43.13.

11. A method for inhibiting growth of a tumor expressing glycoprotein MUC16 in a subject in need thereof, comprising administering to the subject a pharmaceutical composition of claim 6, wherein the tumor is a pancreatic tumor, a colon tumor, an ovarian tumor, a breast tumor, or a liver tumor.

12. The method of claim 11, wherein the method is for the treatment of a cancer.

* * * * *